United States Patent

Ammermann et al.

[11] Patent Number: 6,124,335
[45] Date of Patent: Sep. 26, 2000

[54] FUNGICIDAL MIXTURES

[75] Inventors: Eberhard Ammermann, Heppenheim; Gisela Lorenz, Hambach; Siegfried Strathmann, Limburgerhof; Reinhold Saur, Böhl-Iggelheim; Klaus Schelberger, Gönnheim; Anne van Gastel, Neustadt, all of Germany

[73] Assignee: BASF Aktiengesellschaft, Ludwigshafen, Germany

[21] Appl. No.: 09/155,947

[22] PCT Filed: Apr. 4, 1997

[86] PCT No.: PCT/EP97/01686

§ 371 Date: Oct. 8, 1998

§ 102(e) Date: Oct. 8, 1998

[87] PCT Pub. No.: WO97/37541

PCT Pub. Date: Oct. 16, 1997

[30] Foreign Application Priority Data

Apr. 11, 1996 [DE] Germany .............. 196 14 294

[51] Int. Cl.$^7$ .......... A01N 37/12; A01N 37/18; A01N 37/44; A01N 43/64
[52] U.S. Cl. .......... 514/383; 514/539; 514/619
[58] Field of Search ............... 514/383, 539, 514/619

[56] References Cited

FOREIGN PATENT DOCUMENTS

| 676 031 | 10/1994 | Australia . |
| 398 692 | 11/1990 | European Pat. Off. . |
| 0531837 | 8/1992 | European Pat. Off. . |
| 0645091 | 9/1994 | European Pat. Off. . |
| 0648417 | 9/1994 | European Pat. Off. . |
| 4309272 | 9/1994 | Germany . |

*Primary Examiner*—Allen J. Robinson
*Attorney, Agent, or Firm*—Keil & Weinkauf

[57] ABSTRACT

A fungicidal mixture comprising, as active components, an oxime ether carboxylate of the formula I,

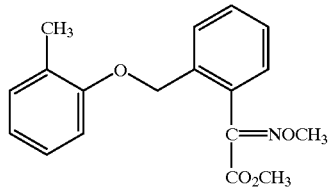

(I)

and an oxime ether carboxamide of the formula II,

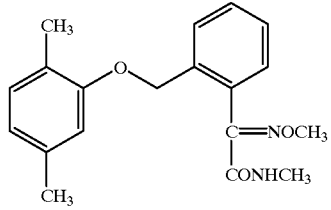

(II)

and also an azole of the formula III

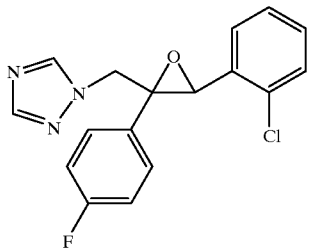

(III)

in a synergistically active amount.

12 Claims, No Drawings

FUNGICIDAL MIXTURES

This application is a 371 of PCT/EP97/01686, filed Apr. 4, 1997.

Description

The present invention relates to a fungicidal mixture which comprises an oxime ether carboxylate of the formula I

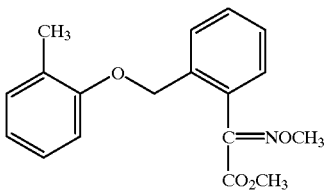

and an oxime ether carboxamide of the formula II,

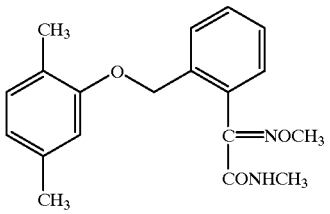

and also an azole of the formula III

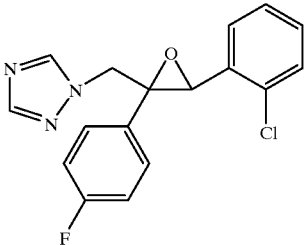

in a synergistically active amount.

Moreover, the invention relates to methods of controlling harmful fungi using mixtures of the compounds I, II and III and to the use of the compound I, II and III for the preparation of such mixtures.

The compounds of the formulae I and II, their preparation and their action against harmful fungi are disclosed in the literature (EP-A 253 213, EP-A 398 692, EP-A 477 631).

Also disclosed is the compound of the formula III, its preparation and its use as fungicide (proposed tradename: Epoxiconazole; EP-A 196 038).

It was an object of the present invention to provide mixtures which have an improved action against harmful fungi combined with a reduced total amount of active ingredients applied (synergistic mixtures) with a view to reducing the rates of application and to improving the spectrum of action of the known compounds.

We have found that this object is achieved by the mixtures defined at the outset. Moreover, we have found that better control of the harmful fungi is possible by applying the compounds I, II and III simultaneously together or separately or when applying the compounds I, II and III in succession than when the individual compounds are used.

In relation to the C=N double bond, the compounds of the formulas I and II can be present in the E or the Z configuration (in relation to the group carboxylic acid function). Accordingly, they can be used in the mixture according to the invention in each case either in the form of the pure E or Z isomer or else in the form of an E/Z isomer mixture. The E/Z isomer mixture or the E isomer is preferably used, the E isomer being especially preferred.

When providing the mixtures, it is preferred to employ the pure active ingredients I, II and III, which can be admixed with other active ingredients against harmful fungi or other pests such as insects, arachnids or nematodes, or else herbidical or growth-regulating active ingredients or fertilizers, as required.

The mixtures of the compounds I, II and III, or the simultaneous use of the compounds I, II and III together or separately are distinguished by an outstanding activity against a broad spectrum of phytopathogenic fungi, in particular from the classes of the Ascomycetes, Deuteromycetes, Basidiomycetes and Phycomycetes. Some of them act systemically and can there also be employed as foliar- and soil-acting herbicides.

They are especially important for controlling a large number of fungi in a variety of crop plants such as cotton, vegetable species (e.g. cucumbers, beans and cucurbits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: Erysiphe graminis (powdery mildew) on cereals, Erysiphe cichoracearum and Sphaerotheca fuliginea on curcubits, Podosphaera leucotricha on apples, Puccinia species on cereals, Rhizoctonia species on cotton, rice and lawns, Ustilago species on cereals and sugar cane, Venturia inaequalis (scab) on apples, Helminthosporium species on cereals, Septoria nodorum on wheat, Botrytis cinera (gray mold) on strawberries, vegetables, ornamental vegetables and grapevines, Cercospora arachidicola on peanuts, Pseudocercosporella herpotrichoides on wheat and barley, Pyricularia oryzae on rice, Phytophthora infestans on potatoes and tomatoes, Plasmopara viticola on grapevines, Pseudoperonospora species on hops and cucumbers, Alternaria species on vegetables and fruit, and Fusarium and Verticillium species.

Furthermore, they can be used in the protection of materials (e.g. the protection of wood), for example against Paecilomyces variotii.

The compounds I, II and III can be applied simultaneously together or separately or in succession, the order in the case of separate application generally not having any effect on the result of the control measures.

The compounds I and II are normally used in a weight ratio of 1:0.1 to 1:10, preferably 1:5 to 1:0.2, in particular 1:3 to 1:0.3 (I:II).

The compounds I and III are normally used in a weight ratio of 1:0.1 to 1:10, preferably 1:0.1 to 1:5, in particular 1:0.2 to 1:3 (I:III).

Depending on the nature of the desired effect, the rate of application of the mixtures according to the invention are from 0.003 to 3.0 kg/ha, preferably 0.02 to 2.0 kg/ha, in particular 0.07 to 1.5 kg/ha.

In the case of the compounds I, the rates of application are from 0.001 to 1.0 kg/ha, preferably 0.05 to 0.5 kg/ha, in particular 0.01 to 0.3 kg/ha.

Accordingly, the rates of application for the compounds II are from 0.001 to 1.0 kg/ha, preferably 0.05 to 0.5 kg/ha, in particular 0.01 to 0.3 kg/ha.

The rates of application for the compounds III are from 0.001 to 1.0 kg/ha, preferably 0.05 to 1.0 kg/ha, in particular 0.05 to 0.5 kg/ha.

For seed treatment, the rates of application of the mixture are generally from 0.001 to 50 g/kg of seed, preferably 0.01 to 10 g/kg, in particular 0.01 to 5 g/kg.

If it is phytopathogenic harmful fungi that are to be controlled, the separate or joint application of the compounds I, II and III or of the mixtures of the compounds I, II and III, is effected by spraying or dusting the seeds, the plants or the soils before or after sowing the plants or before or after plant emergence.

The fungicidal synergistic mixtures according to the invention, or the compounds I, II and III, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guaranteed as fine and uniform a distribution as possible of the mixture according to the invention.

The formulations are prepared in a manner known per se, e.g. by adding solvents and/or carriers. It is usual to admix inert additives such as emulsifiers or dispersants with the formulations.

Suitable surfactants are the alkali metal salts, alkaline earth metal salts and ammonium salts of aromatic sulfonic acids, e.g. ligno-, phenol-, naphthalene- and dibutylnaphthalene sulfonic acid, and of fatty acids, alkyl- and alkylarylsulfonates, alkyl, lauryl ether and fatty alcohol sulfates, and salts of sulfated hexa-, hepta- and octadecanols or of fatty alcohol glycol ethers, condensates of sulfonated naphthalene and its derivates with formaldehyde, condensates of naphthalene, or of the naphthalene sulfonic acids, with phenol and formaldehyde, polyoxethylene octylphenol ether, ethoxylated isooctyl-, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignin-sulfite waste liquors or methylcellulose.

Powders, materials for spreading and dust can be prepared by mixing or jointly grinding the compounds I, II or III or by mixing the compounds I, II and III with a solid carrier.

Granules (e.g. coated granules, impregnated granules or homogeneous granules) are normally prepared by binding the active ingredient, or active ingredients, to a solid carrier.

Fillers or solid carriers are, for example, mineral earths such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I or II, or of the mixture of the compounds I, II and III. The active ingredients are employed in a purity of from 90% to 100%, preferably 95% to 100% (according to NMR or HPLC spectrum).

The compounds I, II or III, or the mixtures or the corresponding formulations, are applied by treating the harmful fungi or the plants, seeds, soils, areas, materials or spaces to be kept free from them with a fungicidally active amount of the mixture, or of the compounds I, II and III in the case of separate application. Application can be effected before or after infection by the harmful fungi.

The fungicidal action of the compounds and of the mixtures is demonstrated by the following experiments:

the active ingredients, separately or together, are prepared as a 20% emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of mixtures of the active ingredients are determined using Colby's formula [R. S. Colby, Weeds 15, 20–22 (1967)] and compared with the observed efficacies. Colby's formula:

$$E = x + y + z - x \cdot y \cdot z / 100$$

E the expected efficacy, expressed in % of the untreated control, when using the mixture of the active ingredients A and B at the concentrations a and b x the efficacy, expressed in % of the untreated control, when using active ingredient A at a concentration of a y the efficacy, expressed in % of the untreated control, when using active ingredient B at a concentration of b z the efficacy, expressed in % of the untreated control, when using active ingredient C at a concentration of c An efficacy of 0 means the infection level of the treated plant corresponds to that of the untreated control plant; an efficacy of 100 means that the treated plants are not infected.

EXAMPLES 1 to 12

Efficacy against Powdery Mildew of Wheat

Leaves of wheat seedlings cv. "Frügold" in pots were sprayed to run-off with aqueous spray mixture prepared with a stock solution of 10% active ingredient, 63% cyclohexanone and 27% emulsifier and, 24 hours after the spray coating had dried on, dusted with spores of powdery mildew of wheat (Erysiphe graminis var. tritici). The test plants were subsequently placed in the greenhouse at temperatures from 20 to 22° C. and 75 to 80% relative atmospheric humidity. After 7 days, the extent of mildew development was determined visually as disease % of the entire leaf area.

The visually determined data for the percentage of diseased leaf area were converted into efficacies as a percentage of the untreated control. An efficacy of 0 is the same disease level as in the untreated control, an efficacy of 100 is a disease level of 0%. The expected efficacies for combinations of active ingredients were determined using Colby's formula (Colby, S. R., Calculating synergistic and antagonistic responses of herbicide Combinations, Weeds, 15, p. 20–22, 1967) and compared with the observed efficacies.

| Ex. | Active ingredient or combinations | Concentration of active ingredient in the spray mixture in ppm | Efficacy in % of the untreated control |
|---|---|---|---|
| 1 V | Control (untreated) | (Disease level 95%) | 0 |
| 2 V | I | 1 | 95 |
|  |  | 0.25 | 0 |
|  |  | 0.06 | 0 |
| 3 V | II | 1 | 84 |
|  |  | 0.25 | 34 |
|  |  | 0.06 | 1 |
| 4 V | III | 0.25 | 34 |
|  |  | 0.06 | 1 |
| 5 V | I + II 1:1 | 1 + 1 | 89 |
| 6 V | I + III 1:1 | 0.25 + 0.25 | 45 |
| 7 V | II + III 1:1 | 0.25 + 0.25 | 84 |

| Ex. | Concentration of active ingredient in the spray mixture | Observed efficacy | Calculated efficacy* |
|---|---|---|---|
| 8 | (I + II) III | 1 + 1 0.06 | 97 | 89 |
| 9 | (I + III) II | 0.25 + 0.25 0.06 | 78 | 46 |
| 10 | (I + III) II | 0.25 + 0.25 0.25 | 89 | 64 |
| 11 | I (II + III) | 0.06 0.25 + 0.25 | 92 | 84 |
| 12 | I (II + III) | 0.25 0.25 | 90 | 84 |

*using Colby's formula

The test results show that the observed efficacy for all mixing ratios exceeds the expected efficacy calculated using Colby's formula.

We claim:
1. A fungicidal mixture comprising, as active ingredients, an oxime ether carboxylate of the formula I

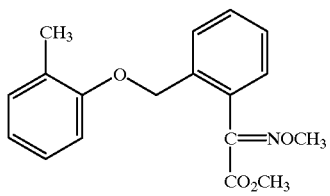

(I)

an oxime ether carboxamide of the formula II

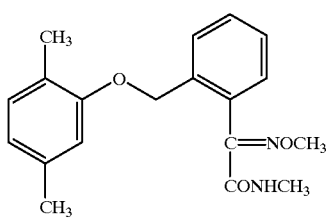

(II)

and an azole of the formula III

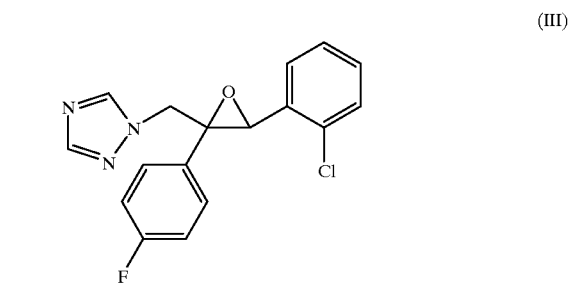

(III)

in synergistically active amounts.

2. A fungicidal mixture as defined in claim 1 wherein the weight ratio of the oxime ether carboxylate I to the oxime ether carboxamide II is 1:0.1 to 1:10.

3. A fungicidal mixture as defined in claim 1 wherein the weight ratio of the oxime ether carboxylate I to the azole III is 1:0.1 to 1:10.

4. A fungicidal mixture as defined in claim 1, wherein the weight ratio of the oxime ether carboxylate I to the oxime ether carboxamide II and to the azole III is 1:10:1, 10:1:1 to 1:1:10.

5. The fungicidal mixture defined in claim 1 which is formulated in two parts, one part comprising the active ingredient I and/or III in a solid or liquid carrier and the other part comprising the active ingredient II in a solid or liquid carrier.

6. The fungicidal mixture of claim 1 which is formulated in two parts, one part comprising the active ingredient I and/or II in a solid or liquid carrier and the other part comprising the active ingredient III in a solid or liquid carrier.

7. A fungicidal mixture as defined in claim 1 which is formulated in three parts, one part comprising the active ingredient I in a solid or liquid carrier, the second part being the active ingredient II in a solid or liquid carrier and the remaining part the active ingredient III in a solid or liquid carrier.

8. A method of controlling harmful fungi, which comprises treating the harmful fungi, their environment, or the plants, seeds, soils, areas, materials or spaces to be kept free from them with a funaicidally effective amount of the ingredient of the formula I as set forth in claim 1, with a synergistically effective amount of the ingredient of the formula II as set forth in claim 1 and with a synergistically effective amount of the ingredient of the formula III as set forth in claim 1.

9. The method of claim 8, wherein the ingredient I and the ingredient II and the ingredient III are applied simultaneously together or separately or in succession.

10. The method of claim 8, wherein the harmful fungi, their environment, or the plants, seeds, soils, areas, materials or spaces to be kept free from them are treated with 0.001 to 1.0 kg/ha of ingredient I.

11. The method of claim 8, wherein the harmful fungi, their environment, or the plants, seeds, soils, areas, materials or spaces to be kept free from them are treated with 0.001 to 1.0 kg/ha of ingredient II.

12. The method of claim 8, wherein the harmful fungi, their environment, or the plants, seeds, soils, areas, materials or spaces to be kept free from them are treated with 0.001 to 1.0 kg/ha of ingredient II.

* * * * *